United States Patent
Held

(10) Patent No.: US 6,730,084 B2
(45) Date of Patent: May 4, 2004

(54) UROLOGICAL RESECTOSCOPE WITH A SPRING BRIDGE

(75) Inventor: Manfred Held, Hamburg (DE)

(73) Assignee: Olympus Winter & Ibe GmbH, Hamburg (DE)

(*) Notice: Subject to any disclaimer, the term of this patent is extended or adjusted under 35 U.S.C. 154(b) by 31 days.

(21) Appl. No.: 10/154,620

(22) Filed: May 23, 2002

(65) Prior Publication Data

US 2002/0183743 A1 Dec. 5, 2002

(30) Foreign Application Priority Data

May 30, 2001 (DE) .......................... 101 26 542

(51) Int. Cl.$^7$ ................................ A61B 18/18
(52) U.S. Cl. ......................... 606/46; 600/101
(58) Field of Search ............... 606/41, 46, 47; 128/898; 600/104–105, 101, 107, 108, 109, 119

(56) References Cited

U.S. PATENT DOCUMENTS

| | | | | |
|---|---|---|---|---|
| 4,955,884 A | * | 9/1990 | Grossi et al. | 606/46 |
| 4,994,062 A | * | 2/1991 | Nishigaki et al. | 606/46 |
| 5,024,212 A | * | 6/1991 | Bonnet et al. | 600/119 |
| 5,088,998 A | | 2/1992 | Sakashita et al. | |
| 5,112,330 A | * | 5/1992 | Nishigaki et al. | 600/143 |
| 5,307,804 A | * | 5/1994 | Bonnet | 600/109 |
| 5,423,795 A | * | 6/1995 | Eckert et al. | 606/1 |
| 5,964,756 A | * | 10/1999 | McGaffigan et al. | 606/41 |
| 6,322,494 B1 | * | 11/2001 | Bullivant et al. | 600/104 |
| 6,514,247 B1 | * | 2/2003 | McGaffigan et al. | 606/41 |

FOREIGN PATENT DOCUMENTS

| | | |
|---|---|---|
| DE | 29 15 271 A1 | 10/1980 |
| DE | 93 03 240.4 U1 | 8/1993 |

OTHER PUBLICATIONS

The Next Step in Resectoscope Technology: 24 Fr. Continuous Flow, Olympus The Visible Dfference, 7.030.129 2: 1/98 Printed in Germany, 4 pages.

* cited by examiner

Primary Examiner—John P. Leubecker
Assistant Examiner—Peter J Vrettakos
(74) Attorney, Agent, or Firm—Rankin, Hill, Porter & Clark LLP

(57) ABSTRACT

A urological resectoscope including a main body carrying a tubular shaft, an optical guide plate arranged at a fixed distance proximally of the main body, a sliding body longitudinally movably guided between the main body and the optical guide plate and a spring bridge comprising two levers connected pivotally together at one end and acted on by a spring, the other ends of which are pivotally connected to the sliding body on the one hand and to the optical guide plate or the main body on the other hand. One of the levers is pivotally connected to only one side of the sliding body.

8 Claims, 2 Drawing Sheets

UROLOGICAL RESECTOSCOPE WITH A SPRING BRIDGE

FIELD OF THE INVENTION

The invention relates to a resectoscope of the type including a main body carrying a tubular shaft, an optical guide plate arranged at a fixed distance proximally of the main body, a sliding body longitudinally movably guided between the main body and the optical guide plate and a spring bridge comprising two levers, which are pivotally connected together at one end and are acted on by a spring and the other ends of which are pivotally connected to the sliding body on the one hand and to the optical guide plate or to the main body on the other hand.

DESCRIPTION OF THE PRIOR ART

Urological resectoscopes of the standard construction which is now usual have an endoscope optical system, which extends through the entire resectoscope including the tubular shaft, and an electrode, generally constructed as a cutting blade, which is longitudinally movably arranged in the region distally in front of the optical system. The electrode is moved by means of an elongate electrode carrier, which projects proximally beyond the region of the tubular shaft and is secured to the sliding body and is electrically connected to the electrode and an electrical power supply. The operator moves the sliding body on the proximal portion of the resectoscope and thus the electrode to produce cutting movements.

In most known resectoscopes, the sliding body is moved against the force of a spring. Several variants are possible in which the sliding body is either pulled back in the proximal direction against the force of a spring or is advanced distally against the force of a spring and then returns automatically under the force of the spring. Finger grip members for actuation can be secured to the main body and to the sliding body or to the sliding body and to the optical system guide plate, depending on the construction. The spring can, depending on the variant referred to above and depending on whether the spring is a compression spring or a tension spring, also be provided between the main body and sliding body or between the sliding body and optical system guide plate. Leaf springs, for instance, are common as the springs.

In resectoscopes of the type referred to above, the spring is constructed in the form of a spring bridge comprising levers and joints. Such a construction is shown in FIG. 21 of U.S. Pat. No. 5,088,998. The two levers are pivotally connected together at a distance from one another by means of two joints on a shaft. Also provided is a spring which urges the two levers apart. The free ends of the two levers are pivotally connected by means of a respective joint centrally beneath the shaft of the resectoscope to the main body on the one hand and to the sliding body on the other hand. The spring bridge is situated beneath the resectoscope in this construction.

A further construction of the type referred to above is shown in the brochure "The Next Step in Resectoscope Technology" from the company Olympus Optical Co. Ltd. dated 1998. The spring bridge is provided in this case above the resectoscope between the sliding body on the one hand and the optical system guide plate on the other hand. In distinction to the construction referred to above, the free ends of the levers laterally engage two bearing points, which are opposed to one another with respect to the optical system, which ensures good rotational stabilisation of the sliding body and makes more expensive sliding guides, as in the construction referred to above, unnecessary.

The spring bridges in the prior art are constructionally very expensive and require very exact mountings in order, in particular, to make the necessary rotational stability possible. The problem of rotational stability is solved in a considerably better manner by the second known construction referred to above. However, a disadvantage of this construction is the mounting of the spring bridge both on the sliding body and also on the optical guide plate with two lateral bearings in each case. The spring bridge is thus mounted on the resectoscope with four bearings which results in a redundancy. If the bearings are machined very precisely in the necessary manner, they tend to jam, which is extremely disadvantageous for precise, sensitive actuation of the resectoscope. Of disadvantage with this known construction are also the high manufacturing costs of the spring bridge with a total of six bearings and also its other constructional expense and its high weight.

The object of the invention is to simplify a resectoscope of the type referred to above structurally and as regards manufacture as regards the construction of the spring bridge to provide good guiding characteristics and to reduce its weight and to produce a construction which does not tend to jam.

SUMMARY OF THE INVENTION

According to the present invention the other end of one of the levers is pivotally connected on only one side of the resectoscope.

In the construction in accordance with the invention, one of the levers engages the resectoscope only on one side. The spring bridge thus engages the resectoscope only with a maximum of three bearings. The redundancy and thus the danger of jamming is, therefore, completely avoided, even with highly precisely fabricated bearings and the construction is simplified. As a result of the reduced number of bearings, the manufacturing and, in particular, the assembly costs are reduced. A resectoscope is produced which may be operated very easily and sensitively with a high stability of guiding, particularly also as regards rotational guidance.

In one embodiment, the other lever is pivotally connected only to the opposite side of resectoscope. Thus both levers are mounted on the resectoscope only on one side, namely on opposite sides. The spring bridge is thus considerably simplified. In particular, both levers may be of the same construction, which reduces the costs.

The two levers could be directly pivotally connected to one another using only one bearing. Advantageously, however, the connected ends of the two levers are pivotally connected to a common shaft and are laterally spaced apart. The proven mode of construction in accordance with the prior art is thus adopted at this position.

The levers may have bearings at their ends and be in the form of rods between the bearings. This mode of construction, which is possible with the present invention, simplifies and facilitates the construction of the levers.

The levers can be inherently straight. Advantageously, however, the other ends of the two levers are constituted by bent portions inclined to the remainder of the lever, the two bent portions being bent in the proximal direction and the distal direction, respectively. The positions of the bearing points may thus be altered in a desired manner. As a result of the bent configuration of the free ends, a better kinematics of the guidance is produced with a higher tilting stability. Rattling as a result of clearances that are present is also prevented.

It is provided in one embodiment that arranged on the optical guide plate there is a distally extending projection to which one of the levers is pivotally connected and which engages in a recess in the sliding body. The bearings at the ends of the free levers may thus be arranged precisely opposite one another with respect to the shaft of the resectoscope without the sliding travel of the sliding body being shortened.

It is also possible that the other lever is pivotally connected to both sides of the main body or the optical guide plate. In this construction the one lever is mounted on the resectoscope with one bearing and the other lever with two bearings. A construction is thus produced with high guiding stability in which redundancy and thus the risk of jamming is reliably prevented.

Further features and details of the invention will be apparent from the following description of certain specific embodiments which is given by way of example with reference to the accompanying drawings.

DESCRIPTION OF THE PREFERRED EMBODIMENTS

Figure 1:
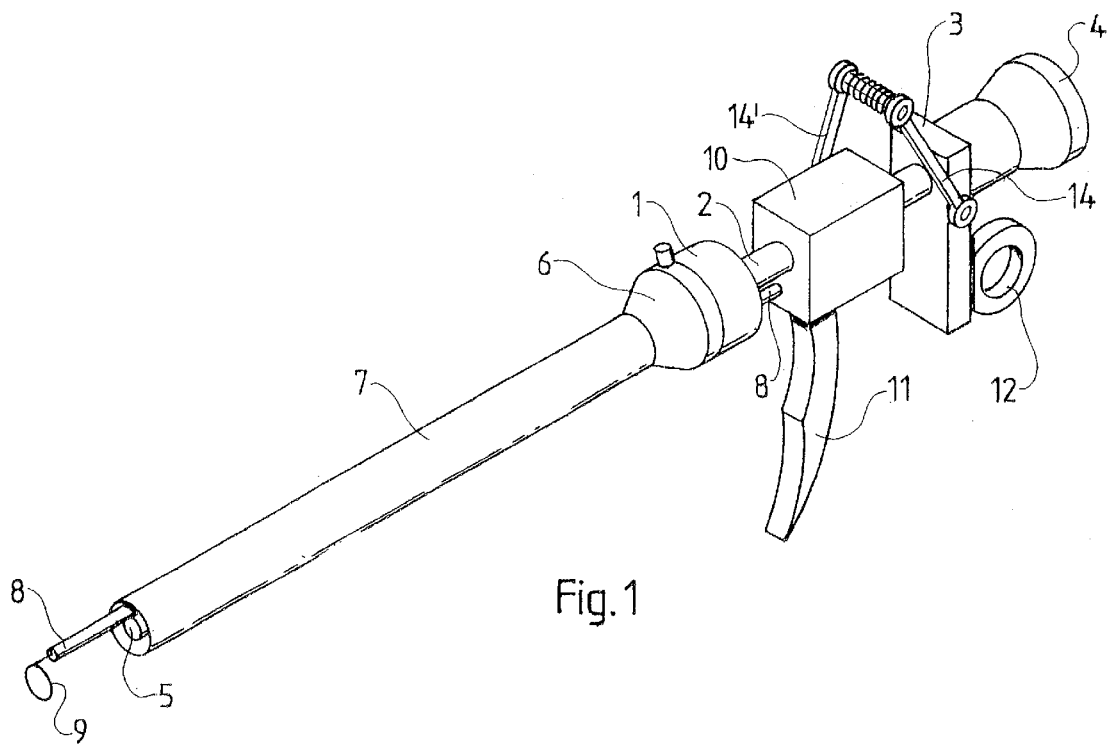
FIG. 1 is a perspective view of a resectoscope in accordance with the invention.
Figure 2:
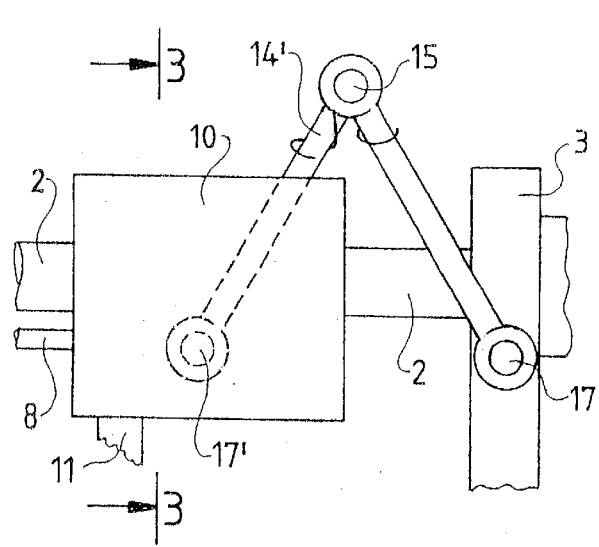
FIG. 2 is a scrap side view of the resectoscope of FIG. 1 showing a region of the spring bridge.
Figure 3:
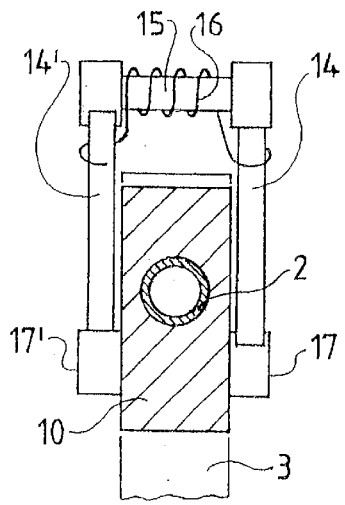
FIG. 3 is a sectional view on the line 3—3 in FIG. 2.

Referring firstly to FIGS. 1 to 3, the resectoscope includes a main body 1 secured to an optical system guide tube 2, secured to which at a proximal spacing from the main body 1 there is also an optical guide plate 3, the purpose of which is well known, namely to guide the optical system and/or to facilitate the introduction of the optical system into the optical system guide tube. An elongate rod-shaped optical system can be introduced through the optical guide tube 2 with an eyepiece 4 at the proximal end and an objective 5 at the distal end. Decouplably connected to the main body 1 with a coupling member 6 is a tubular shaft 7, which surrounds the optical system up to the vicinity of the objective 5.

A rod-shaped electrode carrier 8 extends through the main body 1 and the tubular shaft 7. At its distal end it carries an electrode, which is constructed in the form of a blade 9 in the illustrated exemplary embodiment and which is longitudinally movably arranged in the region in front of the objective 5.

Longitudinally movably arranged on the optical guide tube is a sliding body 10. The sliding body 10 receives the proximal end of the electrode carrier 8, electrically connected to it by means, which are not illustrated, and has further means, which are also not illustrated, for securing it.

The longitudinal movement of the blade 9 required for cutting control is controlled by longitudinal movement of the sliding body 10. This is effected in the illustrated exemplary embodiment by means of a finger grip 11, which is secured to the underside of the sliding body 10, and a thumb ring 12, which is secured to the underside of the optical guide plate 3.

The sliding body 10 and thus the cutting blade 9 are retractable in the proximal direction by exerting a squeezing force on the finger grip 11 and thumb ring 12 against a spring force exerted by a spring bridge, which is constituted by two levers 14 and 14'. The levers are connected to one another by virtue of being pivotally connected at a lateral distance from the optical guide tube 2 (see FIG. 3) to a bearing shaft 15. Extending around the latter is a helical spring 16, the ends of which bear, as shown, on the levers 14 and 14' such that the levers (see FIG. 2) are urged into an open angular position, i.e. the sliding body 10 is urged in the distal direction towards the main body 1.

The free ends of the levers 14 and 14' are connected by means of respective bearings 17 and 17' to one side of the optical guide plate 3 (closest to the viewer in FIG. 2) and to the opposite side (away from the viewer) of the sliding body 10, respectively.

As seen in FIGS. 2 and 3, the levers 14 and 14' are constructed in the form of straight bars between the bearings at their ends. They are both of identical construction.

Figure 4:
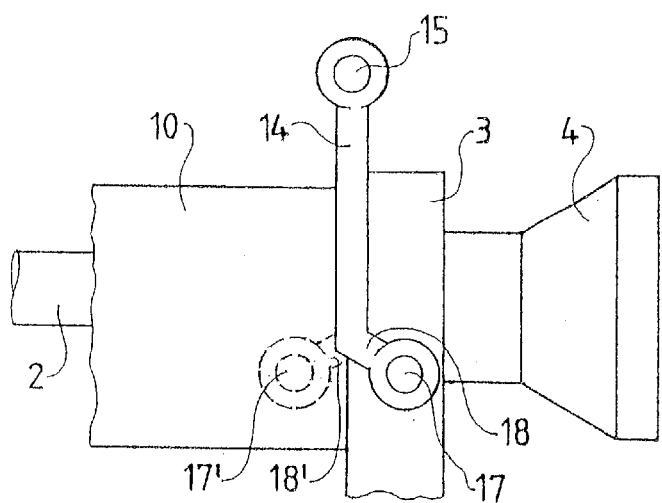
FIG. 4 is a view similar to FIG. 2 of a modified construction.

In the embodiment of FIG. 2, the two levers 14 and 14' are still slightly open, that is to say inclined at a small angle with respect to one another, when the sliding body 10 abuts the optical guide plate 3. This is avoided in the modified construction of FIG. 4 in which the lower end portions 18 and 18' of the levers are angled in the distal and proximal directions, respectively. In the upper region, the two levers 14 and 14' are situated in alignment behind one another, when the resectoscope is viewed from the side, as in FIG. 4, when the sliding body 10 engages the optical guide plate 3.

Figure 5:
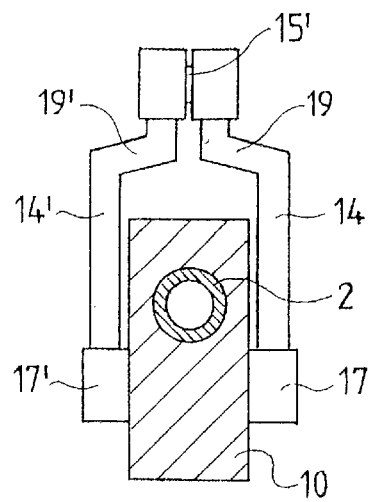
FIG. 5 is a sectional view similar to FIG. 3 of a further modified construction.

FIG. 5 shows a modification in which the upper end portions 19 and 19' of the levers 14 and 14' are bent or cranked towards one another so that they can be mounted directly on one another at 15', that is to say without the intervening bearing shaft 15, as in the embodiment of FIG. 3.

Figure 6:
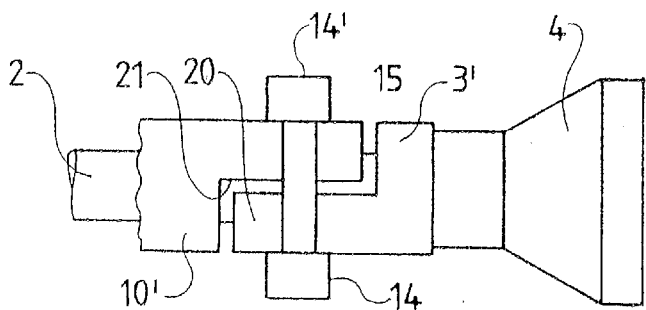
FIG. 6 is a plan view of a further modified construction of resectoscope in accordance with the invention in the region of the spring bridge.

FIG. 6 shows a further modified construction in which the spring bridge corresponds to that in the embodiment of FIGS. 1 to 3. The sliding body 10' and the optical guide plate 3' are, however, of different construction. A projection 20 on the optical guide plate 3' projects in the distal direction into a recess 21 in the sliding body 10'. The bearings for the lower free ends of the straight levers 14 and 14' are situated on the projection 20 and the sliding body 10', respectively. When the sliding body 10' engages the optical guide plate 3', the straight levers 14 and 14' are in alignment, when viewed from the side, even without the bent lower ends 18 and 18', as in FIG. 4.

Figure 7:
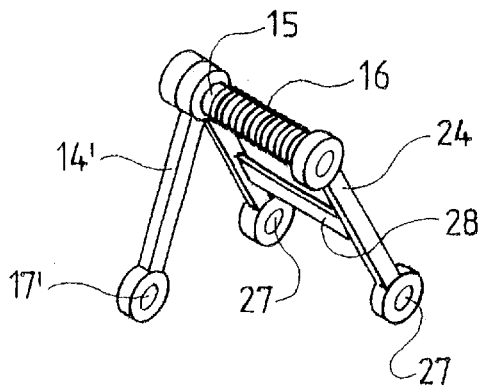
FIG. 7 is a perspective view showing a further construction of spring bridge.

FIG. 7 is a perspective view of a spring bridge in which the lever 14' corresponds to that in the embodiment in FIGS. 1 to 3. The lever 14' is mounted by means of an upper bearing, as in the embodiment described above, on the bearing shaft 15, around which the helical spring 16 is situated. The other lever 24 is, however, of two-arm construction. The arms are connected together by a transverse strut 28 in order to increase stability and have respective upper bearings and lower bearings 27. The two upper bearings are mounted on respective ends of the bearing shaft 15 and, the two bearings 27 are mounted on both sides of the optical guide plate 3, diametrically opposed. A three point mounting is thus produced of the spring bridge on the resectoscope with the three bearings 17', 27, 27.

In the illustrated embodiments, the spring bridge is arranged between the sliding body 10 and the optical guide plate 3. In other embodiments, the spring bridge can also be arranged between the sliding body 10 and the main body 1, with the construction being otherwise the same. Resectoscopes are thus possible of both known types with an "active transporter" and a "passive transporter". The resectoscope shown in FIGS. 1 to 3 corresponds to the construction with an active transporter.

An expanding or opening spring is provided between the levers 14 and 14' in the illustrated embodiments. It can also be a closing spring. Thus, for instance, in the embodiment of FIG. 1, in order to ensure the same operability, instead of a spring bridge with an expanding spring between the sliding body 10 and optical guide plate 3, a spring bridge with a closing spring can be provided between the main body 1 and sliding body 10. Instead of the helical spring 16 shown in the figures, other types of opening or closing spring can be provided between the levers which do not extend around the illustrated bearing shaft 15 but which are provided, for instance, directly between the levers.

In the illustrated embodiments of FIGS. 1 to 6, the two levers 14, 14' engage the endoscope on different sides. In a modification, which is not illustrated, they can, however, be constructed to engage the same side.

Obviously, numerous further modifications and variations of the present invention are possible in the light of the above teachings. It is, therefore, to be understood that within the scope of the appended claims the invention may be practised otherwise than as specifically described herein.

What is claimed is:

1. A urological resectoscope including a main body, a tubular shaft carried by said main body, an optical guide plate arranged at a fixed distance proximally of said main body, a sliding body longitudinally movably guided between said main body and said optical guide plate and a spring bridge, said spring bridge comprising two levers, said two levers being pivotally connected together and being acted on by a spring, one of said two levers being pivotally connected to said sliding body at a first connection location and the other of said two levers being pivotally connected to one of said optical guide plate and said main body at a second connection location, said resectoscope having two sides, wherein the first connection location is disposed on one side of the resectoscope and the second connection location is disposed on the other side of the resectoscope, and wherein the spring bridge is only connected to the sliding body at the first connection location.

2. A resectoscope as claimed in claim 1, wherein said two levers each have first and second ends, and wherein said two levers are pivotally connected to each other at said first ends and are connected to the sliding body and one of said optical guide plate and said main body at said second ends, respectively.

3. A resectoscope as claimed in claim 2, further including a shaft and wherein said two levers are pivotally connected to said shaft and are laterally space apart.

4. A resectoscope as claimed in claim 2, wherein said two levers have respective bearings at said first and second ends and are in the form of rods between said bearings.

5. A resectoscope as claimed in claim 4, wherein said second ends of said two levers comprise bent portions, each said bent portion being inclined to the remainder of the associated lever, said two bent portions being bent in the proximal direction and the distal direction, respectively.

6. A resectoscope as claimed in claim 2, wherein said sliding body defines a recess and said optical guide plate carries a distally extending projection, said projection being adapted to engage in said recess, the second end of one of said two levers being pivotally connected to said projection.

7. A resectoscope as claimed in claim 1, wherein the second end of the other of said two levers is pivotally connected to the optical guide plate at the second connection location.

8. A resectoscope as claimed in claim 7, wherein the other of said two levers comprises a pair of arms connected together by a transverse strut, and wherein the arms have upper bearings, respectively, which comprise the first end of the other of said two levers, and have lower bearings, respectively, which comprises the second end of the other of said two levers, and wherein one of the lower bearings is pivotally connected to the optical guide plate at the second connection location and the other one of the lower bearings is pivotally connected to the optical guide plate at a third connection location, which is disposed on the opposite side of the resectoscope as the second connection location.

* * * * *

UNITED STATES PATENT AND TRADEMARK OFFICE
CERTIFICATE OF CORRECTION

PATENT NO.   : 6,730,084 B2
DATED        : May 4, 2004
INVENTOR(S)  : Manfred Held It is certified that error appears in the above-identified patent and that said Letters Patent is hereby corrected as shown below:

Column 6,
Delete claim 3 in its entirety and replace with:

3. A resectoscope as claimed in Claim 2 said spring bridge further including a bearing shaft and wherein said first ends are pivotally connnected to said bearing shaft at laterally spaced apart bearing locations.
Line 27, delete "claim 1" and replace with -- claim 2 --.
Add claims 9-15:

9. A urological resectoscope including a main body, a tubular shaft carried by said main body, an optical guide plate arranged at a fixed distance proximally of said main body, a sliding body longitudinally movably guided between said main body and said optical guide plate and a spring bridge, said spring bridge comprising two levers, said two levers being pivotally connected together and being acted on by a spring, one of said two levers being pivotally connected to said sliding body at a first connection location and the other of said two levers being pivotally connected to one of said optical guide plate and said main body at a second connection location, said resectoscope having two sides, wherein the first connection location is disposed on one side of the resectoscope and the second connection location is disposed on the other side of the resectoscope, and wherein the spring bridge is connected to the resectoscope only at the first and second connection locations.

10. A resectoscope as claimed in Claim 9, wherein said two levers each have first and second ends, and wherein said two levers are pivotally connected to each other at said first ends and are connected to the sliding body and one of said optical guide plate and said main body at said second ends, respectively.

11. A resectoscope as claimed in Claim 10, said spring bridge further including a bearing shaft and wherein said first ends are pivotally connected to said bearing shaft at laterally spaced apart bearing locations.

12. A resectoscope as claimed in Claim 10, wherein said two levers have respective bearings at said first and second ends and are in the form of rods between said bearings.

13. A resectoscope as claimed in Claim 12, wherein said second ends of said two levers comprise bent portions, each said bent portion being inclined to the remainder of the associated lever, said two bent portions being bent in the proximal direction and the distal direction, respectively.

UNITED STATES PATENT AND TRADEMARK OFFICE
CERTIFICATE OF CORRECTION

PATENT NO. : 6,730,084 B2
DATED : May 4, 2004
INVENTOR(S) : Manfred Held

It is certified that error appears in the above-identified patent and that said Letters Patent is hereby corrected as shown below:

14. A resectoscope as claimed in Claim 10, wherein said sliding body defines a recess and said optical guide plate carries a distally extending projection, said projection being adapted to engage in said recess, the second end of one of said two levers being pivotally connected to said projection.

15. A resectoscope as claimed in Claim 10, wherein the second end of the other of said two levers is pivotally connected to the optical guide plate at the second connection location.

Signed and Sealed this

Twelfth Day of October, 2004

JON W. DUDAS
*Director of the United States Patent and Trademark Office*